United States Patent
Gregorovich et al.

(10) Patent No.: US 6,329,489 B1
(45) Date of Patent: Dec. 11, 2001

(54) PROCESS FOR PRODUCING REACTIVE SILANE OLIGOMERS

(75) Inventors: Basil V. Gregorovich, Wilmington, DE (US); Isidor Hazan, Southfield; Robert R. Matheson, West Bloomfield, both of MI (US); Lech Wilczek, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/467,158

(22) Filed: Dec. 20, 1999

(51) Int. Cl.⁷ .............................. C08G 77/18; C08G 77/24
(52) U.S. Cl. .................. 528/29; 528/26; 528/17; 528/35; 528/12; 528/556; 528/443; 528/444; 528/106; 528/287.16
(58) Field of Search .................. 528/29, 26, 17, 528/35, 12; 556/443, 444; 106/287.16

(56) References Cited

U.S. PATENT DOCUMENTS

| | | | |
|---|---|---|---|
| H1279 | 1/1994 | Stephenson | 524/317 |
| 3,947,386 * | 3/1976 | Prokai et al. | |
| 4,221,697 | 9/1980 | Osborn et al. | 260/42.53 |
| 4,251,576 | 2/1981 | Osborn et al. | 428/331 |
| 4,267,088 | 5/1981 | Kempf | 260/29.2 EP |
| 4,367,313 | 1/1983 | Rizk et al. | 525/102 |
| 4,376,190 | 3/1983 | Schultz et al. | 525/333.1 |
| 4,377,676 | 3/1983 | Gauthier et al. | 528/26.5 |
| 4,413,386 | 11/1983 | Chang et al. | 524/386 |
| 4,446,292 | 5/1984 | Chang et al. | 528/29 |
| 4,467,081 | 8/1984 | Chang et al. | 528/26 |
| 4,501,872 | 2/1985 | Chang et al. | 518/18 |
| 4,565,760 | 1/1986 | Schank | 430/66 |
| 4,613,451 | 9/1986 | Chang et al. | 252/182 |
| 4,652,610 | 3/1987 | Dowbenko et al. | 525/100 |
| 4,678,835 | 7/1987 | Chang et al. | 525/100 |
| 4,732,929 | 3/1988 | Chang et al. | 524/541 |
| 4,766,185 | 8/1988 | Ryntz et al. | 525/479 |
| 4,810,759 | 3/1989 | Ryntz | 525/440 |
| 4,904,504 | 2/1990 | Isozaki et al. | 427/387 |
| 5,051,473 | 9/1991 | Tabuchi et al. | 525/100 |
| 5,066,698 | 11/1991 | Hazan et al. | 424/269 |
| 5,091,460 | 2/1992 | Seto et al. | 524/492 |
| 5,182,174 | 1/1993 | Stephenson et al. | 428/450 |
| 5,190,804 | 3/1993 | Seto et al. | 428/192 |
| 5,219,694 | 6/1993 | Anno et al. | 430/106.6 |
| 5,225,510 | 7/1993 | Bank et al. | 528/12 |
| 5,230,962 | 7/1993 | Stephenson | 428/423.1 |
| 5,244,959 | 9/1993 | Hazan et al. | 524/504 |
| 5,250,605 | 10/1993 | Hazan et al. | 524/504 |
| 5,254,619 | 10/1993 | Ando | 524/504 |
| 5,344,880 | 9/1994 | Nambu et al. | 525/100 |
| 5,369,153 | 11/1994 | Barsotti et al. | 523/429 |
| 5,371,151 | 12/1994 | Berge et al. | 525/377 |
| 5,371,161 | 12/1994 | Knott | 528/9 |
| 5,376,704 | 12/1994 | Barsotti | 523/414 |
| 5,376,706 | 12/1994 | Barsotti et al. | 523/434 |
| 5,391,674 | 2/1995 | Hara et al. | 528/14 |
| 5,399,607 | 3/1995 | Nanbu et al. | 524/385 |
| 5,426,168 | 6/1995 | Witucki | 528/23 |
| 5,431,791 | 7/1995 | December et al. | 204/181.7 |
| 5,455,080 | 10/1995 | van Ooij | 427/470 |
| 5,501,929 | 3/1996 | Kato et al. | 430/49 |
| 5,506,325 | 4/1996 | Swarup et al. | 526/318.41 |
| 5,696,179 | 12/1997 | Chawla | 522/90 |
| 5,719,251 * | 2/1998 | Wilczek et al. | |

FOREIGN PATENT DOCUMENTS

| | | |
|---|---|---|
| 197 36 736 | 2/1999 | (DE) . |
| 0 401 668 | 12/1990 | (EP) . |
| 0 419 669 | 4/1991 | (EP) . |
| 0 900 832 | 3/1999 | (EP) . |
| 0 918 062 | 5/1999 | (EP) . |
| 1095519 | 11/1967 | (GB) . |
| 1510801 | 5/1978 | (GB) . |
| 2 212 163 | 7/1989 | (GB) . |
| 59-168074 | 9/1984 | (JP) . |
| 63-105019 | 5/1988 | (JP) . |
| H3-97734 | 4/1991 | (JP) . |
| 3-139660 | 6/1991 | (JP) . |
| H3-200974 | 9/1991 | (JP) . |
| 4-200681 | 7/1992 | (JP) . |
| 5-8506 | 1/1993 | (JP) . |
| 5-9295 | 1/1993 | (JP) . |
| 5-108676 | 3/1993 | (JP) . |
| 5-101116 | 4/1993 | (JP) . |
| 5-514548 | 6/1993 | (JP) . |
| 6-6833 | 1/1994 | (JP) . |
| 6-47057 | 3/1994 | (JP) . |
| 9-157584 | 6/1997 | (JP) . |
| 9-328652 | 12/1997 | (JP) . |

* cited by examiner

*Primary Examiner*—Robert Dawson
*Assistant Examiner*—Kuo-Liang Peng
(74) *Attorney, Agent, or Firm*—Sudhir G. Deshmukh

(57) ABSTRACT

The invention is directed to a process for making a reactive silane oligomer having low polydispersity, viscosity and volatility. The process utilizes reacting unsymmetrical difunctional silane monomers with water, diol monomers, or a combination thereof to make the reactive silane oligomer. The unsymmetrical difunctional silane monomers are with silane reactive groups having significantly different reactivities. Use of such reactive silane oligomers results in multi-component coating compositions having high miscibility, low VOC, low viscosity and high percentage of solids.

23 Claims, No Drawings

PROCESS FOR PRODUCING REACTIVE SILANE OLIGOMERS

BACKGROUND OF THE INVENTION

This invention concerns a composition comprising reactive silane oligomers having low polydispersity, viscosity and volatility. Such oligomers are useful for multi-component silicon modified organic coatings with low volatile organic content (VOC), improved mar and etch resistance.

A number of clear and pigmented coating compositions are utilized in various coatings, such as, for example, automotive coatings. Such coatings, typically applied as OEM coatings (original equipment manufacturer), are generally solvent based. However, due to increasing concern over the excessive release of volatile organic component (VOC) in the atmosphere, significant research is being conducted for developing low VOC, solvent-based coating compositions, generally with less than 0.6 kilograms of organic solvent per liter of coating composition (5 pounds per gallon), as determined under ASTM D3960 Test.

One of the approaches used in reducing the amount of VOC released by a coating composition during its application on a substrate, such as an automobile body, involves adding a silicon-containing reactive diluent to the coating composition. A number of patents disclose low VOC silicon-containing curable coating compositions, such as, for example, U.S. Pat. No. 4,467,081.

However, none of the approaches disclosed in the prior art improves miscibility in multi-component formulations while still maintaining optimum balance of coating properties, such as good mar and chemical resistance, high gloss and durability. Further limiting factor in the use of silane-based reactive diluents in coating compositions is the poor process control of silane functionalities during the preparation of conventional reactive diluents, which results in a broad distribution of silane functionalities.

The present invention overcomes the foregoing problems, by providing low VOC silane-based coating compositions that result in coatings having improved mar, chemical and environmental etch resistance, appearance and durability while still providing improved miscibility in multi-component formulations, as compared to conventional coating compositions.

STATEMENT OF INVENTION

The present invention is directed to a process for making a reactive silane oligomer, said process comprising:

contacting one or more unsymmetrical difunctional silane monomers with water, with one or more diol monomers, or with a combination thereof, wherein:
said diol monomer is:

$R^1$—(OH)$_2$, wherein $R^1$ is selected from the group consisting of:
a) $C_2$ to $C_{20}$ alkylene, cycloaliphatic rings or aromatic rings, each optionally substituted with at least one member selected from the group consisting of O, N, P and S;
b) two or more cycloaliphatic or aromatic rings connected to each other through a covalent bond, or through an alkylene group of 1 to 5 carbon atoms, or through a heteroatom, or fused together to share two or more carbon atoms, each optionally substituted with at least one member selected from the group consisting of O, N, P and S; and
c) a linear polyester, branched polyester, a combination of said linear and said branched polyesters, polyacrylate, polyolefin, polyether, polycarbonate, polyurethane, or polyamide, each having a GPC weight average molecular weight in the range of from about 200 and 10,000; and said difunctional silane monomer is:

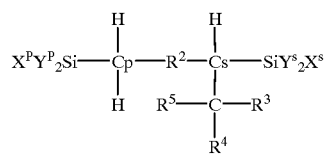

wherein Cp is a primary carbon atom, Cs is a secondary carbon atom and $R^2$ is selected from the group consisting of:
a) $C_3$ to $C_{20}$ alkylene, $C_1$ to $C_{10}$ alkyl substituted cycloaliphatic rings or $C_1$ to $C_{10}$ alkyl substituted aromatic rings, each optionally substituted with at least one member selected from the group consisting of O, N, P and S;
b) $C_1$ to $C_{10}$ alkyl substituted two or more cycloaliphatic rings, or $C_1$ to $C_{10}$ alkyl substituted two or more aromatic rings connected to each other through a covalent bond, or through an alkylene group of 1 to 5 carbon atoms, or through a heteroatom, or fused together to share two or more carbon atoms, each optionally substituted with at least one member selected from the group consisting of O, N, P and S; and
c) a combination of (a) and (b);

$R^3$, $R^4$ and $R_5$ each is independently selected from the group consisting of:
Hydrogen, $C_1$ to $C_{20}$ alkyl, $C_1$ to $C_{10}$ alkyl substituted cycloaliphatic rings or $C_1$ to $C_{10}$ alkyl substituted aromatic rings, each optionally substituted with at least one member selected from the group consisting of O, N, P and S;

$X^P$ and $X^S$ being independently selected from the group consisting of alkoxy containing 1 to 20 carbon atoms, acyloxy containing 1 to 20 carbon atoms, phenoxy, halogen, amine, amide, urea, imidazole, carbamate, ketoximine, oxazolidinone, and a combination thereof; and $Y^P$ and $Y^S$ being independently selected from the group consisting of alkyl containing 1 to 12 carbon atoms, alkoxy containing 1 to 20 carbon atoms, acyloxy containing 1 to 20 carbon atoms, phenoxy, halogen, amine, amide, urea, imidazole, carbamate, oxazolidinone, and a combination thereof;

for producing said reactive silane oligomer having a GPC weight average molecular weight of less than 10,000 and having a polydispersity of less than 3.

The present invention is also directed to a reactive silane oligomer of the formula:

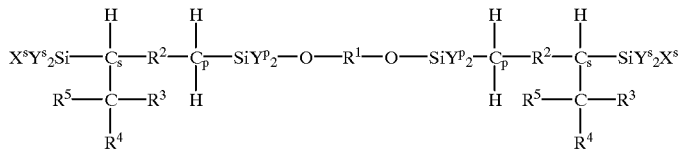

when the unsymmetrical difunctional silane monomer is contacted with the diol monomer in the foregoing process.

The present invention is also directed to a reactive silane oligomer of the formula:

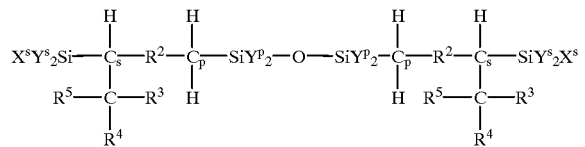

when the unsymmetrical difunctional silane monomer is contacted with water in the foregoing process.

The present invention is further directed to a coating composition containing the reactive silane polymer made in accordance with the foregoing process.

The present invention advantageously provides for a low VOC coating composition having high solids content.

The process of the present invention optimally and efficiently converts the reactants into a reactive silane oligomer having lower polydispersity, viscosity and volatility than a conventional silane oligomer.

The process of the present invention further advantageously produces a reactive silane oligomer having a low GPC weight average molecular weight of less than 10,000. Such a reactive silane oligomer, when included as a reactive diluent in a coating composition, lowers VOC while simultaneously increasing the solids content of the composition. As a result, users can efficiently apply such coating compositions by conventional means, such, as by spraying, dipping, roller coating, brushing or by electro-coating, and still produce durable coatings with low mar, etch and chemical resistance, and glossy appearance on conventional substrates, such automotive bodies.

DETAILED DESCRIPTION OF THE INVENTION

As used herein:

"High solids composition" is a coating composition having more than 40 weight percent, preferably in the range of from 60 to 100 weight percent of total solids based on the total weight of the composition.

"Low VOC composition" is a coating composition having less than 0.6 kilograms of solvent per liter of the coating composition.

"Low viscosity composition" is a coating composition having viscosity in the range of from 1 to 10,000 centipose as measured under ICI cone and plate viscometer.

"GPC weight average molecular weight" means weight average molecular weight as determined by gel permeation chromatography (GPC) using polystyrene standard.

"Polydispersity" means GPC weight average molecular weight divided by GPC number average molecular weight.

"Reactivity" means a degree of chemical activity of silane groups attached to carbon atoms in the backbone of a silane monomer.

"Primary carbon atom (Cp)" is a carbon atom in the backbone, shown below, of an unsymmetrical difunctional silane monomer having only one carbon atom attached to it.

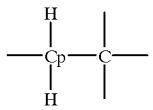

"Secondary carbon atom (Cs)" is a carbon atom in the backbone of the unsymmetrical difunctional silane monomer, shown below, having one hydrogen atom and two carbon atoms attached to it.

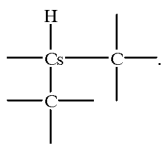

It is believed, without reliance thereon, that the presence of two carbon attached to Cs, due to steric factors, makes the silane groups attached to Cs chemically less reactive than the silane groups attached to Cp. The presence of Cp and Cs, preferably provided with the same silane groups ($SiY_2X$), produces the asymmetric reactivity in the unsymmetrical difunctional silane monomer.

This invention is directed to a process for making reactive silane oligomers having low polydispersity of less than 3. Inclusion of such reactive silane oligomers in a coating composition results in a low VOC coating composition having low viscosity and high solids. The process utilizes unsymmetrical difunctional silane monomers preferably provided with two structurally identical silane reactive groups attached to Cs and Cp for inducing significantly different reactivities, mostly resulting from the steric factors. The process of the invention results in a low dispersity reactive silane oligomer having low GPC weight average molecular weight in the range of 200 to 10,000, preferably in the range of from 400 to 5000, and more preferably in the range of from 500 to 2000. The polydispersity of the reactive silane oligomer is in the range of from 1.1 to 3, preferably in the range of from 1.1 to 1.8, and more preferably in the range of from 1.1 to 1.5.

The process of the invention includes contacting one or more unsymmetrical difunctional silane monomers with one or more diol monomers or with water, or with a combination thereof, to produce the reactive silane oligomer. The preferred reactive silane oligomers are dimers resulting from the reaction of disilane monomers with water and trimers resulting from the reaction of a disilane monomers with diol monomers.

The diol monomer suitable for use in the present invention is typically provided with a hydroxyl equivalent weight in the range of from 30 to 2500, preferably in the range of from 50 to 500 and has the following formula:

$R^1$ group in foregoing formula I may include:
- (a) $C_2$ to $C_{20}$ alkylene; aromatic or preferably cycloaliphatic rings.

Some of the suitable $C_2$ to $C_{20}$ alkylene include ethylene, propylene, butylene, pentylene and hexylene groups.

Some of the suitable cycloaliphatic ring groups include cyclopentylene, cyclohexylene, terpinylene. Cyclohexylene is preferred.

Some of the suitable aromatic ring groups include phenylene, naphtylene, anthracylene.

Each member in the foregoing (a) group may optionally be substituted with at least one member selected from the group consisting of O, N, P and S, N and O are preferred, O is more preferred.

Some examples of the simple diols include 2,3-dimethyl-2,3-butanediol(pinacol), 2,2-dimethyl-1,3-propanediol (neopentyl glycol), 2-ethyl-2-methyl-1,3-propanediol, 2,5-dimethyl-2,5-hexanediol, 1,4-butanediol, 1,6-hexanediol, 1,8-octanediol, 1,10-decanediol, 1,12-dodecanediol, and cycloaliphatic diols such as 1,4-cyclohexanedimethanol, 4,4'-isopropylidenedicyclohexanol, 4,8-bis(hydroxymethyl) tricyclodecane. Neopentyl glycol and cycloaliphatic diols, such as 4,4'-isopropylidenedicyclohexanol are preferred.

$R^1$ may also include:
- (b) 2 to 5, preferably 2 to 3, cycloaliphatic rings or aromatic rings connected to each other through a covalent bond, or through an alkylene group of 1 to 5 carbon atoms, or through a heteroatom, or fused together to share in the range of from 2 to 8 carbon atoms. The cycloaliphatic rings or aromatic rings connected to each other through the alkylene group or the covalent bond are preferred, those connected through the alkylene group are more preferred. The cycloaliphatic rings or aromatic rings suitable for the foregoing group are the same as those described earlier.

Each member in the foregoing (b) group may optionally be substituted with at least one member selected from the group consisting of O, N, P and S. O and N are preferred, O is more preferred.

$R^1$ may also include:
- (c) a linear polyester, branched polyester, a combination of the linear and the branched polyesters, polyacrylate, polyolefin, polyether, polycarbonate, polyurethane, or polyamide group, each having a GPC weight average molecular weight in the range of from about 300 and 10,000, preferably in the range of from 300 to 4000, more preferably in the range of from 300 to 3000.

Linear polyester diols are generally known and are prepared by conventional methods using simple diols known in the art, including but not limited to the previously described simple diols and dicarboxylic acids. Examples of suitable dicarboxylic acids include but are not limited to: hexahydro-4-methylphtalic acid; hexahydrophtalic acid; phtalic acid; isophtalic acid; terephtalic acid; adipic acid; azelaic acid; sebasic acid; succinic acid; maleic acid; glutaric acid; malonic acid; pimelic acid; suberic acid; fumaric acid; and itaconic acid. Anhydrides of the above acids, where they exist, can be also employed and are encompassed by the term "dicarboxylic acids".

In addition, multifunctional monomers which contain both hydroxyl and carboxyl functionalities, or their derivatives are also useful. Such monomers include but are not limited to:

Lactones, such as, caprolactone, butyrolactone, valerolactone, propiolactone; and hydroxyacids, such as, 2-hydroxycaproic acid.

Polyester diols are preferably prepared by first reacting simple diols known in the art, including but not limited to the previously described simple diols, with diacid anhydrides known in the art, including but not limited to the previously described anhydrides. One of the preferred polyester diol is prepared by reacting hexahydromethylphtalic anhydride with water to provide a corresponding dicarboxylic acid. Such a dicarboxylic acid when reacted with an alkylene oxide, preferably with the glycidyl esters of organic acids, such as, for example, CARDURA-E® glycidyl ester, supplied by Shell Chemical Company, Houston, Tex., results in a preferred polyester diol.

Polyether diols are generally known and are prepared by conventional methods, typically by the ring opening polymerization of cyclic ethers, acteals, or a combination thereof. Cyclic ethers are known in the art, such as, for example, epoxides (having a 3 member ring), oxetanes (having a 4 member ring), furanes (having a 5 member ring) and higher cyclic ethers having in the range of from 6 to 10 member rings. Ethylene and propylene oxide and tetrahydrofurane are preferred, tetrahydrofurane is more preferred. Optionally, simple diols, such as, those described previously, may be used for introducing the hydroxyl end groups and for controlling the molecular weight of the polyether diols. Examples of useful polyether polyols include the generally known poly(tetramethylene oxide) diols, available commercially as TERATHANE® poly(tetramethylene oxide) diol, supplied by DuPont Company of Wilmington, Del. TERATHANE® poly(tetramethylene oxide) diol is prepared by polymerizing tetrahydrofurane in the presence of cationic catalysts. Other useful polyether diols also include the poly(propylene oxide) diols prepared by cationic or anionic polymerization or copolymerization of propylene oxide. The simple diols known in the art, including but not limited to the previously described simple diols may be used as initiators or telogens to provide controlled linear structures to the resulting polyether diols.

Linear amide-containing diols are generally known and are typically prepared by analogous processes described previously in the preparation of the polyester diols from any of the aforedescribed diacids, diols or lactones. Additional amounts, in the range of from 10 to 80, preferably in the range of from 20 to 70, all in weight percentages based on the total weight of monomer mixture, of diamines, aminoacids, lactams, or aminoalcohols or a combination thereof are also typically utilized.

Polycarbonate diols are generally known and are prepared conventionally by reacting previously described simple diols with carbonates. Aliphatic polycarbonate diols may also be prepared from 1,3-dioxan-2-one or derivatives thereof. Current conventional methods for the preparation of the aliphatic polycarbonate diols include transesterification of simple diols with lower carbonates of dialkyl preferably having in the range of from 1 to 4 carbon atoms; dioxolanones; or diphenyl carbonates, in the presence of conventional catalysts, such as alkali metal, tin, and titanium compounds.

Polyurethane diols are generally known and are prepared conventionally by reacting previously described simple diols, polyester diols, amide-containing diols, polycarbonate diols, polyhydrocarbon diols with organic polyisocyanates. The organic polyisocyanate can be reacted with the diol either directly to form the polyurethane diol or by the generally known prepolymer method wherein the diol and polyisocyanate are reacted in relative proportion to first produce an isocyanate terminated prepolymer with subsequent reaction of the prepolymer with the same or different additional diol to form the polyurethane diol. The polyisocyanate which is reacted with the diol may be any organic polyisocyanate such as, for example, aromatic, aliphatic, cycloaliphatic, or heterocyclic polyisocyanate, which may be unsubstituted or substituted with alkyl groups, preferably having 1 to 4 carbon atoms. Many such organic polyisocyanates are generally known, examples of which include: toluene diisocyanate isomers, diphenylmethane diisocyanate isomers, biphenyl diisocyanate, tetramethylene-1,4-diisocyanate, hexamethylene 1,6-diisocyanate, isophorone diisocyanate, cyclohexane diisocyanate isomers, hexahydrotoluene diisocyanate isomers and mixtures thereof.

Polyhydrocarbon diols are generally known and are prepared conventionally by polymerizing simple olefins, such as isoprene, butadiene and styrene usually, in the presence of difunctional anionic initiators, followed by hydroxylation with epoxides. Alternatively, such simple olefins may be polymerized in the presence of multifunctional cationic initiators for monomers, such as isobutylene or styrene, followed by hydroxylation of olefin terminal groups. Polyhydrocarbon diols are generally known and available commercially, as KRATON LIQUID® polyhydrocarbon diol, supplied by Shell Chemical Company, Houston, Tex.

Most preferred diol monomers include 1,4 cyclohexane dimethanol, hydrogenated bisphenol A, or a combination thereof.

The unsymmetrical difunctional silane monomers suitable for use in the present invention has a weight average molecular weight in the range of from 300 to 1500, preferably in the range of from 350 to 1000. It is of the following formula:

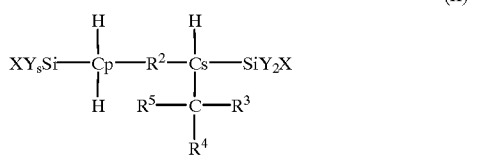

(II)

In formula II, Cp is a primary carbon atom and Cs is a secondary carbon atom. $R^2$ in formula II is selected from one or more of following:

a) $C_3$ to $C_{20}$ alkylene, $C_1$ to $C_{10}$ alkyl substituted cycloaliphatic rings or $C_1$ to $C_{10}$ alkyl substituted aromatic rings, Each member in the foregoing (a) group may optionally be substituted with at least one member selected from the group consisting of O, N, P and S. O and N are preferred, O is more preferred.

b) $C_1$ to $C_{10}$ alkyl substituted two or more cycloaliphatic rings, or $C_1$ to $C_{10}$ alkyl substituted two or more aromatic rings connected to each other through a covalent bond, or through an alkylene group of 1 to 5 carbon atoms, or through a heteroatom, or fused together to share two or more carbon atoms, Each member in the foregoing (b) group may optionally be substituted with at least one member selected from the group consisting of O, N, P and S. O and N are preferred, O is more preferred; and c) a combination of (a) and (b).

Preferred (a) in the foregoing $R^2$ are cyclohexylene and terpinylene, more preferred being cyclohexylene.

Preferred (b) in the foregoing $R^2$ is norbornylene.

$R^3$, $R^4$ and $R^5$ each is independently selected from the group consisting of:

Hydrogen, $C_1$, to $C_{20}$ alkyl, $C_1$ to $C_{10}$ alkyl substituted cycloaliphatic rings or $C_1$ to $C_{10}$ alkyl substituted aromatic rings, each optionally substituted with at least one member selected from the group consisting of O, N, P and S, O and N are preferred and O is more preferred.

$X^P$ and $X^S$ each in formula II is independently selected from the group consisting of alkoxy containing 1 to 20 carbon atoms, acyloxy containing 1 to 20 carbon atoms, phenoxy, halogen, amine, amide, urea, imidazole, carbamate, ketoximine, imidazole, oxazolidinone, and a combination thereof.

$Y^P$ and $Y^S$ each in formula II is independently selected from the group consisting of alkyl containing 1 to 12 carbon atoms, alkoxy containing 1 to 20 carbon atoms, acyloxy containing 1 to 20 carbon atoms, phenoxy, halogen, amine, amide, urea, imidazole, carbamate, ketoximine, oxazolidinone, and a combination thereof. Alkoxy is preferred and methoxy is more preferred.

Examples of the preferred unsymmetrical difunctional silane monomers include but are not limited to bis (trimethoxysilyl) derivatives of the following polyolefins: limonene and other terpines, 4-vinyl-1-cyclohexene, 5-vinyl-2-norbornene. The preferred unsymmetrical difunctional silane monomers include 4-(2-trimethyoxysilylethyl)-1-trimethoxysilylcyclohexane, 5-(2-trimethoxysilylethyl)-trimethoxysilyl norbornane, or a combination thereof.

When the diol monomers are contacted with the unsymmetrical difunctional silane monomers in accordance with the process of the present invention, resulting reactive silane oligomers usually contain variable levels, generally in the range of from 1 to 100 weight percent, preferably in the range of from 3 to 80 weight percent based on the total weight of monomer mixture of their corresponding hydrolysis and condensation products from the reaction with water, which may be added purposely or may be adventitiously introduced from the ambient moisture or with other components, particularly with the diol monomers whose commercial grades usually contain significant levels of water. As a result of the aforedescribed hydrolysis/condensation processes more stable —Si—O—Si— linkages are advantageously introduced in the resulting reactive silane oligomer along with an increase in weight average molecular weight, and a relative reduction in viscosity compared over convention reactive silane oligomers prepared from symmetrical disilane monomers The oligomerization of the diol monomers with the difunctional silane monomers resulting in the C—O—Si formation is an equilibrium process. As a result, the output of the process can be controlled to achieve higher yield of the desired $R^1$—C—O—Si—$R^2$ by using a stoichiometric excess of the difunctional silane monomers, removing a volatile X-H byproduct from the reaction mixture, or by utilizing both of the foregoing steps.

The silylation/oligomerization of the diol with disilane monomers usually results in a complex mixture composed of various oligomers and isomers, shown by mass spectrographic analysis. This is due to the random nature of the silylation involving multifunctional reactants and a contribution of the silane hydrolysis/condensation processes, usually due to the adventitious formation of water. An attractive coating property balance invention, such as scratch, chemical etch resistance and appearance, of a coating composition containing the reactive silane oligomer of the present invention is often obtained by a narrow operational window of a specific product mixture composition. The oligomer composition can be varied widely by the molar ratio of the reactants and the extent of the oligomerization controlled by the catalyst choice, reaction time and reaction temperature.

Thus, the process of the present invention may be further improved by any one or a combination of the following steps for producing the reactive silane oligomers:

I. By adjusting the reactivity ratio (Cp/Cs) between the silane groups ($XY_2Si$—) attached to Cp and Cs in the range of from 1.1 to 100,000, preferably in the range of 1.1 to 10,000, more preferably in the range of from 2 to 1000. It was unexpectedly discovered that by utilizing the difference between the higher reactivity of the silane group attached to the Cp and the lower reactivity of the identical silane group attached to the Cs, the reactive silane oligomers of the present invention are produced. The reactivity ratio may be further increased by substituting one or more hydrogen atoms on carbon atoms connected to Cs with moieties selected from the group consisting of $C_1$ to $C_{20}$ alkyl or aryl groups, or a combination thereof. $C_1$ to $C_{20}$ alkyl groups are preferred.

II. By adjusting the molar ratio of difunctional silane monomer to hydroxy groups in the range from 0.7 to 4, preferably in the range of from 0.7 to 3, more preferably in the range of from 0.9 to 1.4 wherein said molar ratio means the ratio between:

i) the difunctional silane monomers and 2 times water,
ii) the difunctional silane monomers and 2 times the diol monomers, or
iii)

$$\frac{\text{difunctional silane monomers}}{2 \text{ (water and diol monomers)}}.$$

III. By increasing the conversion of the unsymmetrical difunctional silane monomers into the reactive silane oligomer in the range of from 50 percent to 100 percent, preferably in the range of from 60 percent to 95 percent, more preferably in the range of from 65 percent to 90 percent. The foregoing increase in the conversion is accomplished by increasing the catalyst reactivity and concentration, increasing the reaction temperature during the oligomerization, and increasing the reaction time.

IV) By utilizing a combination of said steps I, II, and III.

The reaction may be carried out with or without a catalyzing amount of a catalyst, primarily depending on the reactivity of the SiX. The catalyzing amount of the catalyst used is typically in the range of from 0.01 percent to 5 percent, preferably in the range of from 0.01 percent to 2 percent and more preferably in the range of from 0.01 percent to 0.5 percent, all in weight percentages based on the total weight of starting reaction mixture. It is desired for the storage stability, particularly moisture stability to prepare the reactive silane oligomer essentially free of a catalyst. Therefore, catalysts which can be effectively and conveniently removed from the products, by conventionally means, such as ion exchange or absorbing media, are preferred. Particularly useful catalysts include heterogeneous catalysts, such as, fluoroalkylsulfonic acid NAFION® NR-50 supplied by DuPont Company of Wilmington, Del., which can be easily separated from the product. Other preferred catalysts are volatile catalysts, such as, trifluoroacetic acid; amines or thermofugitive catalysts, such as, tetraalkylammonium hydroxides, which can be substantially removed by a postheating. Many other useful catalysts can be employed and can be optionally removed by passing the product through an appropriate ion exchange or absorbing media. Examples of other useful catalysts include but are not limited to, essentially any medium or strong acids with pKa below 8, preferably in the range of from 2 to 5, such as, sulfonic acids; alkali bases; ammonium salts; tin containing compounds, such as, dibutyltin dilaurate, dibutyltin diacetate, dibutyltin dioctoate and dibutyltin dioxide; titanates, such as, tetraisopropyl titanate, TYZOR® tetrabutyl titanate supplied by DuPont Company of Wilmington, Del., aluminum titanate; aluminum chelates, and zirconium chelate.

Typically the silylation reaction is conducted in a substantially moisture free atmosphere, usually under a blanket of an inert dry gas, such as nitrogen. The reaction mixture which includes the diol and disilane monomers, optionally with a catalyst, is heated for several hours, typically in the range of from 3 to 8 hours, at a temperature ranging from 60° C. to 200° C. with the distillation and removal of the low boiling, volatile reaction byproduct, such as an alcohol, typically methanol. The progress of reaction is monitored by measuring the amount of the byproduct alcohol collected, reaction mixture viscosity changes, and optionally by substrate conversion and product formation by using conventional gas chromatography, nuclear mass resonance and mass spectroscopy. Optionally, to minimize color in the resulting reactive silane oligomer, some conventional methods may be employed, such as, by adding anti-color additives containing active P-H groups to the reaction mixture or by filtration of the reaction mixture through active carbon, silica or other standard decolorizing media. To reduce the VOC of the resulting reactive silane oligomer, the process of the invention is preferably carried in the absence of solvent. However, to further reduce the viscosity of the oligomer, a small amount, generally less than 50 percent by weight percent based on the total weight of composition of an organic solvent, such as aliphatic hydrocarbon, preferably methylethyl ketone, xylene, ether, ester may be added. Typically, the reactive silane oligomer made by the process of the present invention useful for high solids coatings has viscosity in the range of from 1 to 10,000, preferably in the range of from 10 to 5000, more preferably in the range of from 10 to 5000, all in centipoise as measured by using ICI cone and plate viscometer supplied by Gardner Laboratory.

The reactive silane oligomers are generally storage stable. To enhance the storage stability, the reactive silane oligomers are preferably stored in airtight containers to prevent the introduction of moisture. Thus, conventional moisture scavengers, such as, orthoformates, orhtoacetates or some alcohols, preferably propanol or butanol may optionally be added to further extend the storage stability. The storage stability may be further enhanced by storing the reactive silane oligomers in sealed containers under dry inert gas, such as, nitrogen. Moreover, it is desired for improved storage stability to have the stored reactive silane oligomers to be essentially free of any catalyst that were used during the oligomerization process.

The present invention is also directed to a reactive silane oligomer made according to the process of the invention. Thus, a reactive silane oligomer of the following formula is obtained when the unsymmetrical difunctional silane monomer is contacted with the diol monomer:

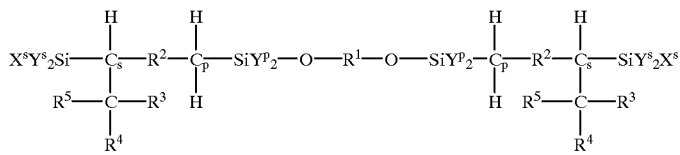

A reactive silane oligomer of the following formula is obtained when the unsymmetrical difunctional silane monomer is contacted with water:

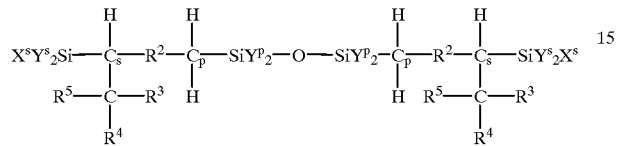

Reactive silane oligomer mixtures, particularly first order homologs enriched in low molecular weight oligomers, preferably with GPC weight average molecular weight in the range of from 500 to 3000 are preferred.

The present invention is further directed to a coating composition, such as, an automotive coating composition, containing the reactive silane oligomer, as a reactive diluent. Typically, the coating composition contains in the range of from 3 to 90, preferably in the range of from 10 to 90 and more preferably in the range of from 20 to 80, all in weight percentages based on the total weight of the composition of the reactive silane oligomer to produce a coating composition having high solids in the range of from 40 percent to 100 percent, preferably in the range of from 50 percent to 100 percent and more preferably in the range of from 60 percent to 100 percent; low viscosity in the range of from 10 to 3000, preferably in the range of from 10 to 2000 and more preferably in the range of from 10 to 1000, all in centipoise. By using the reactive silane oligomers of the present invention in a multi-component coating composition, the degree of miscibility of the multiple polymeric components of such a coating composition is significantly improved.

The coating composition containing the reactive silane monomer may contain additional conventional additives in suitable amounts. Such additives include pigments, stabilizers, rheology control agents, flow agents, toughening agents and fillers. The use of such additional additives will, of course, depend on the intended use of the coating composition. Fillers, pigments, and other additives that would adversely effect the clarity of the cured coating will not be included if the composition is intended as a clear coating.

The reactive silane oligomers made in accordance with the process of this invention is suitable for coating compositions containing a variety of conventional binders, such as, acrylic polymers as solutions or dispersions; polyisocyanates; polyolefins, polyesters.

If desired, the coating compositions containing the reactive silane oligomer may also include conventional co-solvents, generally organic solvents in amounts that do not produce high VOCs. Some of such solvents are aromatic hydrocarbons, such as, petroleum naphtha or xylenes; ketones, such as, methyl amyl ketone, methyl isobutyl ketone, methyl ethyl ketone or acetone; esters, such as, butyl acetate or hexyl acetate; and glycol ether esters, such as, propylene glycol monomethyl ether acetate.

The reactive silane oligomers are particularly suitable for coating compositions used in automotive OEM and refinishes, as primers, basecoats, undercoats and overcoats. These oligomers may be also used as reactive diluents in high solids coating compositions used in marine applications, maintenance coatings, or coating compositions, such as those used in coating metal substrates, such as steel and aluminum or non-metallic substrates, such as, wood and concrete.

EXAMPLES AND PROCEDURES

Example 1 (Difunctional Silane Monomer 1)

A 2-neck 100 ml round-bottom flask was equipped with a magnetic stirring bar, heating mantle, solids addition funnel, and condenser. The condenser was fitted with a Claisen adapter and a polytetrafluoroethylene-clad thermocouple was inserted through the Claisen adapter and condenser to reach the liquid layer of the flask. The other arm of the Claisen adapter was connected to a 50 ml liquid addition funnel fitted with a Dewar condenser. The entire assembly was purged with nitrogen prior to the reaction and a positive pressure of nitrogen was maintained during the reaction.

The round bottom flask was charged with 4-vinyl-1-cyclohexene (22 g, 0.20 mole). The solids addition funnel was charged with 3g of Vazo® 64 initiator, supplied by DuPont Company of Wilmington, Del. The liquid addition funnel was charged with trichlorosilane (57 g, 0.42 mole). The condenser on the flask and the condenser on the solids addition funnel were cooled to −10° C. Stirring was started and the flask contents were heated. Once the flask temperature exceeded 90° C., enough trichlorosilane was added to bring the flask temperature to about 85° C. Small quantities of Vazo® 64 initiator from the solids addition funnel were added intermittently to the reaction mixture. The temperature was maintained between 85–95° C. by adding trichlorosilane and small amounts of the initiator as needed.

Excess trichlorosilane in the reaction mixture was evaporated by passing nitrogen over the reaction mixture and recondensing trichlorosilane in the liquid addition funnel. At this point, the temperature was allowed to rise to 125° C., then held for 1 hour. The total reaction time was 15 hours. The reaction mixture was then cooled to ambient temperature and the product isolated by standard inert atmosphere techniques. After isolation, the GC analysis, using decane as an internal standard, indicated that the vinylcyclohexene was consumed giving both monosubstituted product: 4-(2-trichlorosilylethyl)cyclohex-1-gene and isomers thereof and disubstituted product: 4-(2-trichlorosilylethyl)-1-trichlorosilylcyclohexane and isomers thereof. Bis (trimethoxysilylated) reactive monomer, namely 4-(2-trimethoxysilylethyl)-1-trimethoxysilylcyclohexane (4-VCHSi$_2$), was obtained by a conventional methoxylation of the reaction mixture and then isolated by a vacuum distillation.

Example 2 (Difunctional Silane Monomer 2)

A mixture of 5-vinyl-2-norbornene (100 g, 0.83 mole), trichlorosilane (320 g, 2.36 mole) and platinum divinyl complex supplied by Gelest, Inc., of Tullytown, Penn. (0.6 g 2–3% in xylene) was heated in a pressure reactor at 115° C. for 4 hours. The excess trichlorosilane was stripped under vacuum. A gas chromatography analysis showed the disilylated product purity to be greater than 96%. To the reaction product, a mixture of anhydrous methanol (115 g, 3.6 mole) and trimethylorthoformate (530 g, 5.0 mole) was added dropwise under vacuum. After the addition was complete, triethylamine (15 g, 0.15 mole) was added and the reaction mixture was refluxed for 2 hours. The volatiles were distilled off and the solids were filtered off. The reaction mixture was distilled at 80–100° C. under a vacuum of 0.03–0.10 Torr, collecting about 10% of the first fraction (forecut). A gas chromatography, mass spectroscopy (K+IDS) and IH NMR analysis indicated the products having the desired disilane structure with >97% purity composed of four isomers in Mw/Mn=1.45 (as determined by Matrix Assisted Laser Desorption Ion Mass Spectroscopy (MALDI MS), color of a=−0.79,=+3.8 (as determined by Minolta Colorimeter).

The following is a representative reaction mechanism, based on the foregoing Example 3 for specific oligomerization providing a narrow polydispersity oligomer mixture enriched in low oligomers and particularly the desired reactive silane trimer, which was a 4-(2-trimethoxysilylethyl)-1 trimethoxysilylcyclohexane/hydrogenated bisphenol A (hereafter-VCH-$Si_2$/HBPA/VCH-$Si_2$):

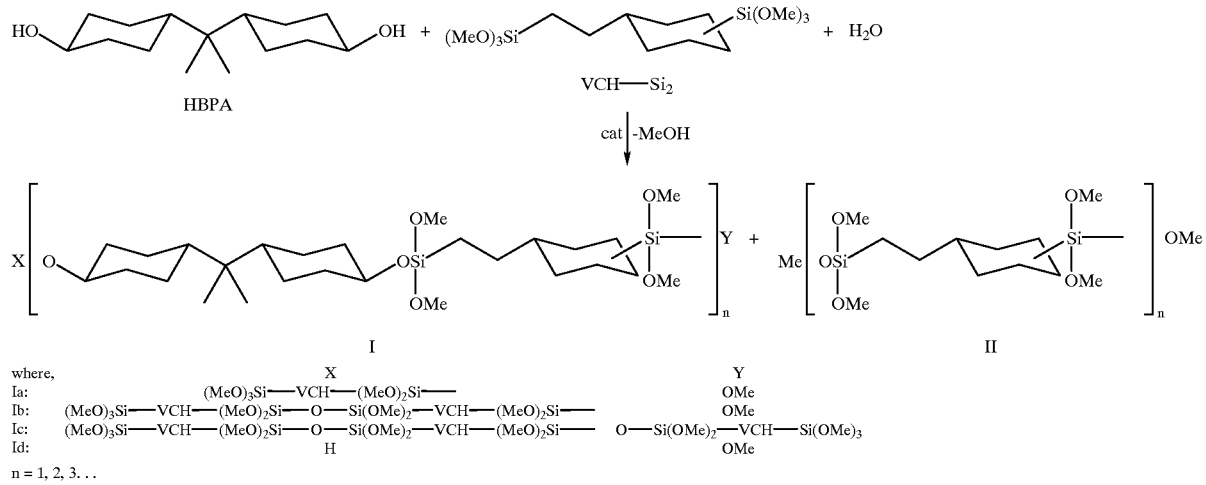

Scheme 1
Hybrid silane reactive oligomers in the VCH—$Si_2$/HBPA/$H_2O$ system.

ratio 7/1/3/1 (measured by GC). The monomer obtained, namely 5-(2-trimethoxysilylethyl)-trimethoxysilylnorbornane, (280 g) was a colorless liquid having a viscosity of <0.1 poise at room temperature.

Oligomer of Example 3

In a five-liter flask equipped with a magnetic stirrer, Vigreux 287300 fractional distillation head, supplied by Kontes under a nitrogen blanket, a reaction mixture of hydrogenated bisphenol A HBPA (700 g, 2.91 mole), difunctional silane monomer 1 of Example 1 above-(2400 g, 6.82 mole of 1 420-VCH-$Si_2$), Nafion® NR-50 (100 g) catalyst supplied by DuPont Company of Wilmington, Del. and trifluoroacetic acid (TFAA, 5 g) was heated at 100–120° C. After about 6 hours, the pot temperature was increased from 105 to 119° C. and about 240 ml MeOH was collected as a byproduct. The resulting crude reaction product had a viscosity of 12 poise, color a=−1.3,=+6.4 (as measured by Minolta Colorimeter). The crude product was diluted with about 500 ml hexanes, filtered through a multilayer system composed of: a Whatman 50 filter paper supplied by VWR Scientific Products of Philadelphia, Penn.: silica gel desiccant, grade 12 (EM-SX0143J-3); silica gel 60 (EM#9385-3) supplied by VWR Scientific Products; decolorizing carbon supplied by VWR Scientific Products, Norit 211 (EK-1133099) supplied by VWR Scientific Products. Volatiles were removed in 1 hour at 75° C. under vacuum (20 Torr) on a rotarye-vaporator supplied by VWR Scientific Products. The resulting reactive silane oligomer obtained by reacting the diol with the difunctional silane monomer and water had a yield of 2700 g, viscosity of 15 poise, Mn=1750, MALDI and LDI MS analysis revealed that the reactive silane oligomers were composed of 5 homologue series with several major components (>2%) of molecular weights in the 350–3000 range (Example 3, Table 1). Data indicated that the final products were combinations of two VCH-$Si_2$ silane oligomers, i.e., by silication of HBPA and by hydrolysis/condensation with adventitious $H_2O$ shown in Scheme 1.

Although MALDI discriminates against low molecular mass components, combined with GC, it gave a good approximation of the oligomeric composition. The reactive hybrid oligomers contain 13 major components (>2 wt %) (Example 3, Table 1), which represented 5 homologue series (Scheme 1). There are three oligomer classes, i.e., unreacted VCH-$Si_2$ (~25 wt %), HBPA/VCH-$Si_2$ oligomers ($\Sigma$Ia+Id~50 wt %) and $H_2O$/NVCH-$Si_2$ oligomers ($\Sigma$Ib+Ic+II(n$\geq$) ~25 wt %). The oligomerization process was not complete, because ~6% hydroxyl groups of HBPA remained unsilylated in the Id oligomers. At higher conversions, oligomer viscosity drastically increased, which is detrimental for coating reproducibility and VOC. There are three types of reactive bonds to the silicon, which determine the reactivity/stability balance of the hybrid oligomers, i.e., original Si-$OCH_3$ (88.5 mol %), Si-OC(cyclohexyl in HBPA) (9.3 mol %) and Si-OSi (2.2 mol %) from adventitious $H_2O$, which were in the 1/0.11/0.025 molar ratio, respectively.

The oligomers had a narrow polydispersity (Mw/Mn<1.5 by MALDI at Mn=1800), which is critical for high solids/low viscosity balance and good compatibility with other coating composition components. The key to achieving the narrow Mw/Mn is a selective oligomerization pattern due to the asymmetrical VCH-$Si_2$ structure, which had two trimethoxysilyl groups of different reactivities. The silicon group attached to the primary carbon atom (Cp)was significantly more reactive than the silyl group connected to the secondary carbon atom (Cs) of the cyclohexane ring.

Table 1 shows the major components (>2%) of the silane reactive oligomers in the VCH-Si$_2$/HBPA/H$_2$O system, as determined by MALDI MS (Scheme 1) of example 3.

TABLE 1

Example 3

| Oligomer | II | Id | II | Ia | II | Id | Ib | Ia | Ic | Ib | Ia | Ib | Ia |
|---|---|---|---|---|---|---|---|---|---|---|---|---|---|
| DP (n) | 1 | 1 | 2 | 1 | 3 | 2 | 1 | 2 | 1 | 2 | 3 | 3 | 4 |
| M. W. | 352 | 560 | 658 | 880 | 964 | 1088 | 1186 | 1408 | 1492 | 1714 | 1936 | 2242 | 2464 |
| (wt %) | 23[a] | 2.7 | 9.5 | 28 | 3.4 | 2.4 | 4.8 | 11 | 2.1 | 3.6 | 5.5 | 1.9 | 2.5 |
| (mol %) | 46 | 3.4 | 10 | 22 | 2.5 | 1.6 | 2.8 | 5.5 | 1.0 | 1.5 | 2.0 | 0.6 | 0.7 |
| SiOCH$_3$[b] | 27.4 | 1.7 | 0.1 | 22.3 | 3.4 | 1.4 | 3.9 | 7.6 | 1.8 | 2.6 | 3.5 | 1.2 | 1.5 |
| SiOCHBPA | 0 | 0.3 | 0 | 4.5 | 0 | 0.3 | 0.6 | 1.6 | 0.2 | 0.4 | 0.8 | 0.2 | 0.3 |
| SiOSi[b] | 0 | 0 | 1.0 | 0 | 0.5 | 0 | 0.3 | 0 | 0.2 | 0.1 | 0 | 0.1 | 0 |

[a]by GC
[b]SiOCH$_3$ (mol %) = 100%xSiOCH$_3$/3xΣSi (mol/mol)
SiOCHBPA (mol %) = 100%xSiOCHBPA/3xΣSi (mol/mol)
SiOSi (mol %) = 100%xSiOSi/3xΣSi (mol/mol)
[c]Dp (n) degree of polymerization

Oligomers of Examples 4–16

The procedure described earlier in Example 3 was followed in preparing the oligomers of Examples 4–16 shown in Table 2 below, where Component I (as in Scheme 1, shown above) is 4-VCH-Si$_2$/HBPA.

TABLE 2

| Ex. | A | B[a] | C[a] | D | E | F[b] | G[c] | H[c] | I | J | K[d] |
|---|---|---|---|---|---|---|---|---|---|---|---|
| 4 | 1.17 | 3.1 | 0.19 | 119 | 6 | | | | | | |
| | | | | 85 | 22 | | 73 | | 22 | | 1.8 |
| 5 | 1.17 | 3.1 | 0.19 | 120 | 5 | 86 | | | | | |
| | | | | 120 | 7 | 89 | 66 | 0.87 | 14 | 3.9 | 1.2[f] |
| 6 | 1.17 | 3.1 | 0.19 | 120 | 3 | 82 | | | | | |
| | | | | 120 | 5 | 86 | 64 | 0.87 | 12 | 2.7 | 0.7[f] |
| 7 | 1.20 | 0.77 | 0.77 | 120 | 5 | 87 | | | 5.6 | 6.5 | |
| | | | | 120 | 8 | 89 | 65 | 0.88 | 7.0 | 7.6 | 1.8 |
| 8 | 1.20 | | 0.77 | 120 | 5 | 84 | | | 6.2 | 7.5 | |
| | | | | 120 | 8 | 89 | 61 | 0.82 | 7.0 | 10.1 | 1.6 |
| 9 | 1.20 | | 0.15 | 142 | 2 | 82 | | | 4.9 | 3.1 | |
| | | | | 142 | 5 | 87 | 60 | 0.83 | 7.3 | 6.6 | 0.8 |
| 10 | 1.20 | | 0.15 | 135 | 5 | 87 | | | 5.0 | 2.1 | |
| | | | | +0.15 P-H[f] | 136 | 9 | 90 | 60 | 0.80 | 7.6 | 2.7 | 0.5[e] |
| 11 | 0.78 | 0.50 | 0.10 | 140 | 2 | 78 | 80 | 0.80 | 83 | 2.9 | 0.3 |
| 12 | 0.90 | 0.50 | 0.10 | 120 | 5 | 66 | | | 18 | | |
| | | | | 95 | 8 | 73 | 75 | 0.9 | 30 | 2.6 | 0.8 |
| 13 | 1.10 | 3.8 | 0.15 | 120 | 5 | 87 | | | 15 | 4.7 | |
| | | | | 120 | 8 | 90 | 82 | 0.99 | 19 | 5.5 | 2.7 |
| 14 | 1.15 | 3.8 | 0.15 | 120 | 5 | 87 | | | 10 | 6.9 | |
| | | | | 120 | 8 | 90 | 75 | 0.96 | 15 | 8.9 | 3.7 |
| 15 | 1.20 | 3.8 | 0.15 | 120 | 5 | 89 | | | 8.0 | 5.8 | |
| | | | | 120 | 8 | 92 | 72 | 0.94 | 12 | 8.0 | 3.1 |
| 16 | 1.25 | 3.8 | 0.15 | 120 | 5 | 86 | | | 5.4 | 6.6 | |
| | | | | 120 | 8 | 89 | 73 | 1.03 | 7.8 | 8.5 | 3.1 |

Ex. means Examples
A Molar ratio of disilane to hydroxyls of diol monomers
B Catalyst
C Catalyst co-component (TFA)
D Reaction temperature in degrees Centigrade
E Reaction time in hours
F byproduct in weight percentage formed during oligomerization
G VCH weight percentage conversion
H VCH/OH conversion ratio
I oligomer viscosity in poise
J (b) color reading of crude oligomer
K (b) color reading of filtered oligomer TABLE 2-continued

| Ex. | A | B[a] | C[a] | D | E | F[b] | G[c] | H[c] | I | J | K[d] |
|---|---|---|---|---|---|---|---|---|---|---|---|

[a]Nafion ® NR-50 catalyst; TFA = CF$_3$CO$_2$H both supplied by DuPont Company of Wilmington, Delaware
[b]MeOH yield (%) = MeOH collected/2XHBPA (mole/mole) × 100%
[c]VCH conversion (%) by GC; VC/OH = VCH conversion/MeOH yield (mole/mole)
[d]color value after filtration through carbon/celite/silica/filter paper
[e]color value after filtration through celite/silica/filter paper only
[f]color value with Decolorizer added (P-H = 9,10-dihydro-9-oxa-10-phosphaphenanthrene-10-oxide)

The forgoing Table 2 illustrates that the oligomer composition and properties, such as optical clarity can be varied widely by varying the molar ratio and the extent of the oligomerization as controlled by the catalyst choice, reaction time and temperature.

The procedure described earlier in Example 3 was followed in preparing the oligomers of Examples 17–20 shown in Table 3 below, where Component I (as in Scheme 1, shown above) is 4-VCH-Si$_2$/HBPA.

TABLE 3

| Ex. | A | B[a] | C | D | E | F[b] | G[c] | H | I | J[d] |
|---|---|---|---|---|---|---|---|---|---|---|
| 17 | 1.20 | 0.26 | 105 | 5 | 68 | | | 4.8 | 1.3[f] | |
| | | (Me) | 110 | 7 | 71 | | | 5.2 | 1.1[f] | |
| | | | 140 | 9 | 75 | 59 | 0.94 | 6.3 | 1.4[f] | 0.5 |
| 18 | 1.20 | 0.30 | 107 | 5 | 79 | | | 5.1 | 1.2[f] | |
| | | (Me) | 145 | 8 | 85 | 53 | 0.75 | 5.6 | 1.1[f] | 0.5[e] |
| | | /MS | | | | | | | | |
| 19 | 1.20 | 0.19 | 106 | 5 | 74 | | | 6.0 | 1.3[f] | |
| | | (Bu) | 135 | 7 | 81 | 58 | 0.86 | 8.1 | 2.5[f] | 0.10 |
| 20 | 1.20 | 0.19 | 110 | 5 | 79 | | | 5.3 | 1.0 | |
| | | (Bu) | 110 | 7 | 80 | | | | 0.9 | |
| | | /MS | 138 | 8.5 | 84 | 61 | 0.87 | 7.3 | 1.2 | 0.02 |

Ex. means Examples
A Molar ratio of disilane to hydroxyls of diol monomers
B Catalyst
C Reaction temperature in degrees Centigrade
D Reaction time in hours
E byproduct in weight percentage formed during oligomerization
F VCH weight percentage conversion
G VCH/OH conversion ratio

TABLE 3-continued

| Ex. | A | B[a] | C | D | E | F[b] | G[c] | H | I | J[d] |
|---|---|---|---|---|---|---|---|---|---|---|

H oligomer viscosity in poise
I (b) color reading of crude oligomer
J (b) color reading of filtered oligomer
[a]$R_4NOH$, where R = Me, Bu
MS = purified over molecular sieves
[b]MeOH yield (%) = MeOH collected/2X HBPA (mole/mole) × 100%
[c]VCH conversion (%) by GC
VC/OH = VCH conversion/MeOH yield (mole/mole)
[d]color value after filtration through carbon/celite/silica/filter paper
[e]color value after filtration through celite/silica/filter paper only
[f]hazy From the forgoing data, it is seen that the reactive silane oligomers of the present invention having low polydispersity are produced when the control of the molar ratios between the difunctional silane monomers, water and the diol monomers as well as the reactivity ratio of disilane to hydroxyls (Cp/Cs) in the claimed ranges is utilized. Furthermore, higher the molar ratio, lower will be the viscosity. By including such oligomers in a coating composition, its viscosity is reduced and its miscibility is improved.

Oligomer of Example 21

A mixture of bis(trimethoxysilyl)-limonene (470 g, 1.24 mole), water (16 g, 0.89 mole) and dodecylbenzenesulfonic acid amine salt (5.0 g) was reacted for 12 hours at room temperature Volatiles (57.6 g) were removed under vacuum. The cloudy reaction product was diluted with 500 ml of anhydrous hexanes and filtered through dry silica gel 60 and dry decolorizing activated carbon under nitrogen. Volatiles were removed under vacuum. The filtered reaction product was a colorless liquid having viscosity of 6.4 poise, containing<7% starting monomer, as measured by GC, a dimer as a major component and a small amount of trimer, as measured by KIDS mass spectroscopy. The reactive silane oligomers obtained by reacting disilylated limonene with water showed significantly enhanced solids residue at 93.6% vs. that of the starting monomers, when small samples were heated for 1 hour at 100° C. (220° F.). Additional reactive silane oligomers were also made by using the foregoing process where the viscosities were measured at 1.0, 1.4, 3.2, 5.2, 6.1, 14, 15 and 16 in poises.

Oligomer of Example 22

A mixture of 5-(2-trimethoxysilylethyl)-trimethoxysilylnorbornane (290 g, 0.80 mole), water (9.0 g, 0.50 mole) and dodecylbenzenesulfonic acid amine salt (3.0 g) was reacted for 12 hours at room temperature. Volatile were removed under vacuum. The cloudy reaction product was diluted with 300 ml of anhydrous hexanes and filtered through dry silica gel 60 and dry decolorizing activated carbon under nitrogen. Volatiles were removed under vacuum. A yield of 170 g the filtered reaction product was obtained. It was a colorless liquid having a viscosity of 1.6 poise, containing<15% of starting monomers, as measured by GC, a dimer as a major component and a small amount of trimer, as measured by KIDS mass spectroscopy. The reactive silane oligomers obtained by reacting 5(2-trimethoxysilylethyl)-trimethoxysilylnorbornane with water showed significantly enhanced solids residue vs. that of the starting monomers, when small samples were heated for 1 hour at 100° C. (220° F.). Additional reactive silane oligomers were also made by using the foregoing process where the viscosities were measured at 1.2 and 1.5 in poises.

Oligomer of Example 23

To a two-liter, three-neck flask, equipped with a magnetic stirrer, reflux condenser, addition funnel under nitrogen blanket, a reaction mixture of 2-trimethoxysilylethyl-trimethoxysilylcyclohexane (930 g, 2.66 mole) and dodecylbenzenesulfonic acid aminopropanol salt (10 g) was added. With stirring, the contents of the flask were heated at 70° C. and water (32 g, 2.0 mole) was added dropwise at the rate 4 g/10 min. After the addition of 16 g water, the reaction mix became cloudy. Nafion® NR50 (3.7 g) catalyst was added and then the remaining 16 g water was added over the 10 minutes. The reaction was continued at 70° C. for another 12 hours. Volatiles (157 g) were removed at 80° C. under vacuum. The cloudy reaction product was diluted with 400 ml anhydrous hexanes and filtered through dry silica gel 60 (EM Science # 9385-3) and dry charcoal (activated Darco G-60, EM Science # CX0645-1). Volatiles were removed under vacuum. A yield of 483 g of almost colorless filtered reaction product was obtained. It was a liquid having a viscosity of 4.3 poise containing 4% starting disilane, as measured by GC. The reactive silane oligomers obtained by reacting 2-trimethoxysilylethyl-trimethoxysilylcyclohexane with water showed significantly enhanced solids residue vs. that of the starting monomers, when small samples were heated for 1 hour at 100° C. (220° F.). Additional reactive silane oligomers were also made by using the foregoing process where the viscosities were measured at were 0.6, 0.8, 1.2, 1.6, 2.1 and 3.2 in poises

What is claimed is:

1. A process for making a reactive silane oligomer, said process comprising:

contacting one or more unsymmetrical difunctional silane monomers with water, with one or more diol monomers, or with a combination thereof, wherein:

said diol monomer is:

$R^1$—$(OH)_2$, wherein $R^1$ is selected from the group consisting of:
  a) $C_2$ to $C_{20}$ alkylene, cycloaliphatic rings or aromatic rings, each optionally substituted with at least one member selected from the group consisting of O, N, P and S;
  b) two or more cycloaliphatic or aromatic rings connected to each other through a covalent bond, or through an alkylene group of 1 to 5 carbon atoms, or through a heteroatom, or fused together to share two or more carbon atoms, each optionally substituted with at least one member selected from the group consisting of O, N, P and S; and
  c) a linear polyester, branched polyester, a combination of said linear and said branched polyesters, polyacrylate, polyolefin, polyether, polycarbonate, polyurethane, or polyamide, each having a GPC weight average molecular weight in the range of from about 200 and 10,000; and said difunctional silane monomer is:

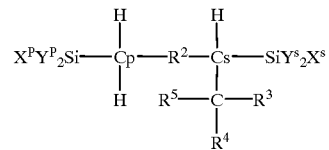

wherein Cp is a primary carbon atom, Cs is a secondary carbon atom and
$R^2$ is selected from the group consisting of:
  a) $C_3$ to $C_{20}$ alkylene, $C_1$ to $C_{10}$ alkyl substituted cycloaliphatic rings and $C_1$ to $C_{10}$ alkyl substituted aromatic rings, each optionally substituted with at least one member selected from the group consisting of O, N, P and S;

b) $C_1$ to $C_{10}$ alkyl substituted two or more cycloaliphatic rings, or $C_1$ to $C_{10}$ alkyl substituted two or more aromatic rings connected to each other through a covalent bond, or through an alkylene group of 1 to 5 carbon atoms, or through a heteroatom, or fused together to share two or more carbon atoms, each optionally substituted with at least one member selected from the group consisting of O, N, P and S; and c) a combination of (a) and (b);

$R_3$, $R^4$ and $R^5$ each is independently selected from the group consisting of:

hydrogen, $C_1$ to $C_{20}$ alkyl, $C_1$ to $C_{10}$ alkyl substituted cycloaliphatic rings or $C_1$ to $C_{10}$ alkyl substituted aromatic rings, each optionally substituted with at least one member selected from the group consisting of O, N, P and S;

$X^P$ and $X^S$ being independently selected from the group consisting of alkoxy containing 1 to 20 carbon atoms, acyloxy containing 1 to 20 carbon atoms, phenoxy, halogen, amine, amide, urea, imidazole, carbamate, ketoximine, oxazolidinone, and a combination thereof; and $Y^P$ and $Y^S$ being independently selected from the group consisting of alkyl containing 1 to 12 carbon atoms, alkoxy containing 1 to 20 carbon atoms, acyloxy containing 1 to 20 carbon atoms, phenoxy, halogen, amine, amide, urea, imidazole, carbamate, oxazolidinone, and a combination thereof;

for producing said reactive silane oligomer having a GPC weight average molecular weight of less than 10,000 and having a polydispersity of less than 3.

2. The process of claim 1 further comprising:

I. adjusting the reactivity ratio (Cp/Cs) between the silane groups ($XY_2Si$—) attached to Cp and Cs in the range of from 1.1 to 100,000;

II. adjusting the molar ratio of difunctional silane monomer to hydroxy groups the range of from 0.7 to 4 wherein said molar ratio means the ratio between:
i) said difunctional silane monomers and 2 times water,
ii) said difunctional silane monomers and 2 times said diol monomers, or
iii)

$$\frac{\text{difunctional silane monomers}}{2 \text{ (water and diol monomers)}};$$

III. increasing in the range of from 50 percent to 100 percent the conversion of said unsymmetrical difunctional silane monomers into said reactive silane oligomer; or IV) utilizing a combination of said steps I, II. and III.

3. The process of claim 2 wherein said reactivity ratio is increased by substituting one or more hydrogen atoms on carbon atoms connected to Cs with moieties selected from the group consisting of $C_1$ to $C_{20}$ aryl and alkyl and a combination thereof.

4. The process according to claim 1 wherein said unsymmetrical difunctional silane monomer has a molecular weight in the range of from 300 to 1500.

5. The process according to claim 1 wherein said diol monomer has a GPC weight average molecular weight of less than 3,000.

6. The process according to claim 1 wherein said unsymmetrical difunctional silane monomer is 4-(2-trimethoxysilylethyl)-1-trimethoxy-silylcylohexane, 5-(2-trimethoxysilylethyl)-trimethoxysilylnorbornane, bis (trimethoxysilylated) limonene, or a combination thereof.

7. The process according to claim 1 wherein said diol monomer is hydrogenated bisphenol A, cyclohexane dimethanol, or a combination thereof.

8. The process according to claim 1 wherein said unsymmetrical difunctional silane monomer is contacted with said diol monomer, water or a combination thereof, in the presence of a catalyzing amount of a catalyst.

9. The process according to claim 8 wherein said catalyst is selected from the group consisting of fluorosulfonic acid, fluoroalkyl sulfonic acid, trifluoroacetic acid, tetraalkylammonium hydroxide, ammonium hydroxide, sulfonic acid, dibutyltin dilaurate, dibutyltin diacetate, dibutyltin dioctoate, dibutyltin dioxide, tetraisopropyl titanate, tetrabutyl titanate, aluminum titanate; aluminum chelate, and zirconium chelate.

10. The process according to claim 8 wherein said catalyzing amount of said catalyst is in the range of from 0.01 percent to 5 percent, all in weight percentages based on the total weight of reaction mixture.

11. The process according to claim 8 further comprising separating said catalyst from said reactive silane oligomer.

12. A reactive silane oligomer made in accordance with the process of claim 1,2,3,4,5,6,7,8,9,10 or 11.

13. The reactive silane oligomer of claim 12 is of the formula:

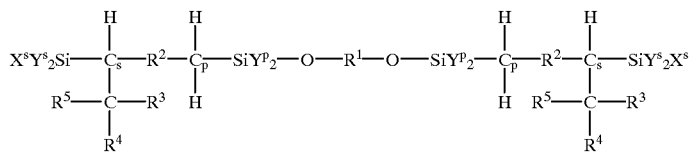

when said unsymmetrical difunctional silane monomer is contacted with said diol monomer.

14. The reactive silane oligomer of claim 12 is of the formula:

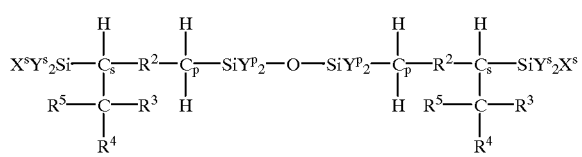

when said unsymmetrical difunctional silane monomer is contacted with water.

15. A coating composition having a low viscosity and low VOC comprising a reactive silane oligomer made in accordance with the process of claim 1,2,3,4,5,6,7,8,9, 10 or 11.

16. The reactive silane oligomer of claim 13 when 4-(2-trimethoxysilylethyl)-1-trimethoxysilylcyclohexane is contacted with hydrogenated bisphenol A and water.

17. The reactive silane of claim 14 when bis (trimethoxysilyl)-limonene is contacted with water.

18. The reactive silane of claim 14 when 5-(2-trimethoxysilylethyl)-trimethoxysilylnorbornane is contacted with water.

19. The reactive silane of claim 14 when 4-(2-trimethoxysilylethyl)-1-trimethoxysilylcyclohexane is contacted with water.

20. The process of claim 1 wherein a GPC weight average molecular weight of said reactive silane oligomer ranges from 200 to 10,000.

21. The process of claim 1 wherein the GPC weight average molecular weight of said reactive silane oligomer ranges from 500 to 2000.

22. The process of claim 1 wherein the polydispersity of said reactive silane oligomer ranges from 1.1 to 3.

23. The process of claim 1 wherein the polydispersity of said reactive silane oligomer ranges from 1.1 to 1.5.

* * * * *

UNITED STATES PATENT AND TRADEMARK OFFICE
CERTIFICATE OF CORRECTION

PATENT NO.   : 6,329,489 B1  Page 1 of 1
DATED        : December 11, 2001
INVENTOR(S)  : Gregorovich et al.

It is certified that error appears in the above-identified patent and that said Letters Patent is hereby corrected as shown below:

<u>Column 1,</u>
Line 46, replace "group the range" with -- group in the range --.

Signed and Sealed this

Eleventh Day of February, 2003

JAMES E. ROGAN
*Director of the United States Patent and Trademark Office*